United States Patent [19]

Quinn, III

[11] 4,226,030
[45] Oct. 7, 1980

[54] SUBJECT IDENTIFICATION SYSTEM WITH OVERLIE COVER

[76] Inventor: William T. Quinn, III, 681 Park Ave., Freehold, N.J. 07728

[21] Appl. No.: 943,428

[22] Filed: Sep. 18, 1978

[51] Int. Cl.³ .......................................... G09B 1/04
[52] U.S. Cl. .................................................. 35/28
[58] Field of Search ................ 35/27, 28, 62, 75, 53, 35/54; 40/490

[56] References Cited

U.S. PATENT DOCUMENTS

| | | | |
|---|---|---|---|
| 3,353,281 | 11/1967 | Schulze | 35/28 |
| 4,047,307 | 9/1977 | Quinn | 35/28 |

FOREIGN PATENT DOCUMENTS 1137088  12/1968  United Kingdom ....................... 35/28

Primary Examiner—Harland S. Skogquist
Attorney, Agent, or Firm—Sughrue, Rothwell, Mion, Zinn and Macpeak

[57] ABSTRACT

An identification system has a flexible wallet in which a composite of subject component segments are selectably assembled. The wallet has a back panel which is slotted to define a backing panel, and the components are inserted through the slots to abut an inward locator. A cover panel is hingedly connected to the back panel, and may be tinted in flesh tones to color the assembled subject.

4 Claims, 3 Drawing Figures

U.S. Patent    Oct. 7, 1980    4,226,030
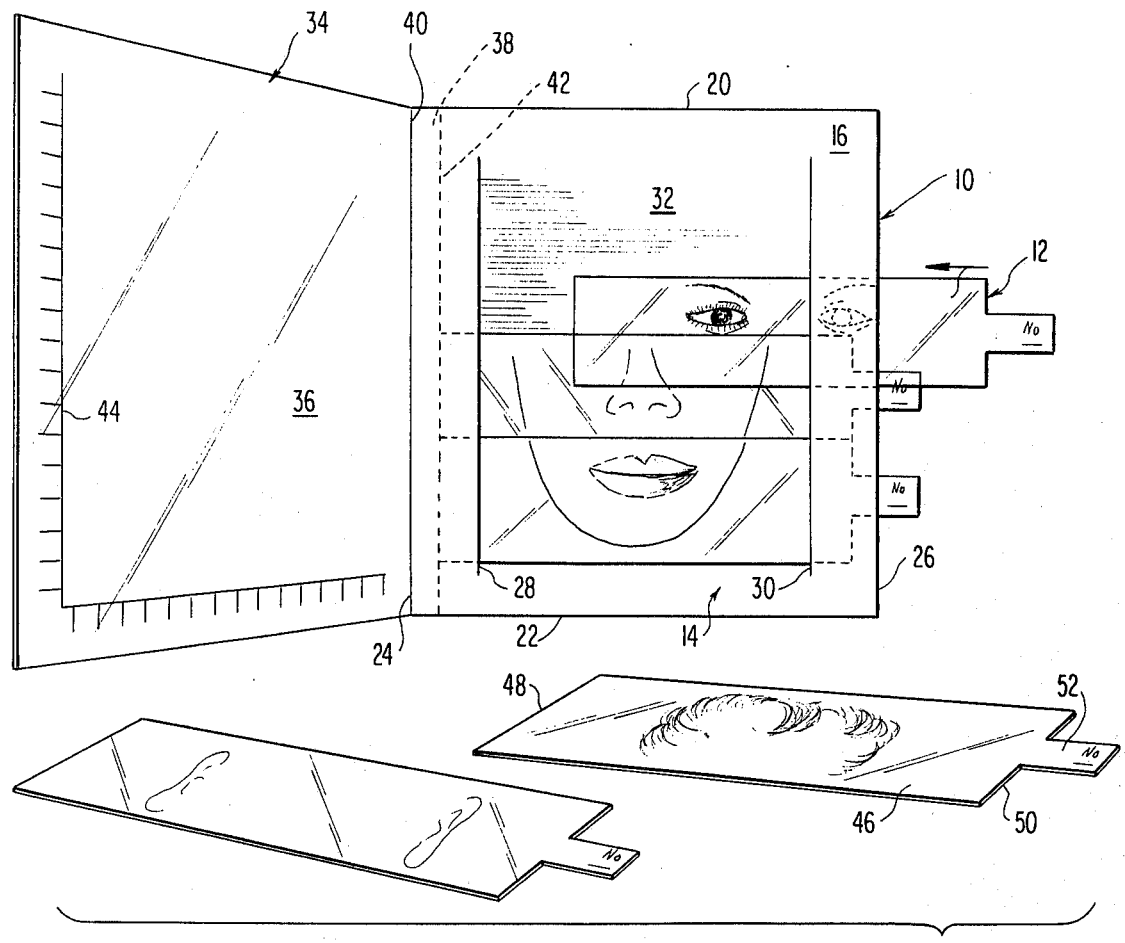
FIG.1
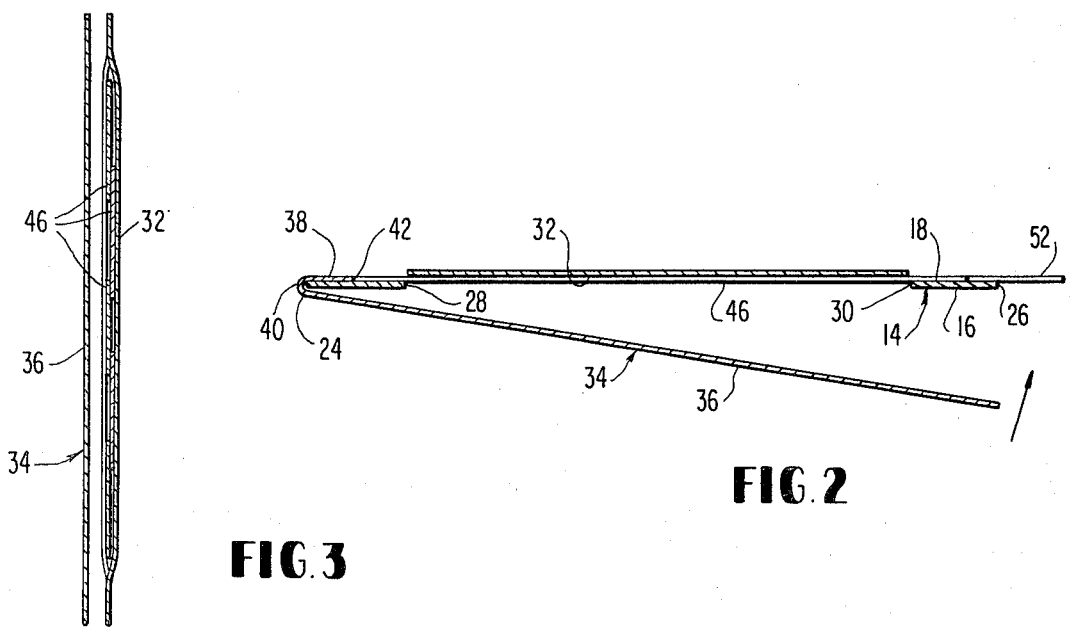
FIG.2
FIG.3

SUBJECT IDENTIFICATION SYSTEM WITH OVERLIE COVER

BACKGROUND OF THE INVENTION

1. Field of the Invention

This invention pertains to improvements in facial identification systems employed in police and other identification agency activities.

2. Statement of the Prior Art

This invention is related to that type of identification means shown in my prior U.S. Pat. Nos. 3,896,565 and 4,047,307 and in my co-pending application Ser. No. 832,045, now U.S. Pat. No. 4,114,293.

SUMMARY OF THE INVENTION

Facial identification systems generally have come into widespread use by police and security agencies. The effectiveness of these systems depends in large measure on providing a witness with an opportunity to assist the system operator in assembling the likeness as soon as possible following an occurrence. The means provided by this invention is extremely compact and is also of a very simple nature, leading to reduced cost and increased availability. Thus, more units may be acquired without budgetary increases, leading to maximum utilization.

The system hereof proposes a wallet or folder having an opaque back and a transparent front. The back has means for changeable insertion and temporary support of a series of feature component strips. The cover may be positioned over the assembled unit, and is of a material tending to hold the components in place when superposed thereover.

Another objective is to provide means for applying skin tone to the assembled facial representation.

Other and further objects and advantages will become apparent to those skilled in the art from a consideration of the following specification when read in conjunction with the annexed drawing.

BRIEF DESCRIPTION OF THE DRAWING

FIG. 1 is a partially disassembled perspective view showing facial representation components and a holder constructed and assembled in accordance with the teachings of this invention;

FIG. 2 is a transverse sectional view along the line indicated by the arrow in FIG. 1; and FIG. 3 is a vertical cross-section.

DESCRIPTION OF THE PREFERRED EMBODIMENT

The invention comprises a wallet or folder 10, and a series of feature components 12 which are releaseably and selectively engaged therein.

The folder 10 includes a back member 14 formed of a opaque flexible plastic material. The member 14 is substantially rectangular, and has opposite inner and outer faces 16 and 18. By way of reference herein, the back member includes a top edge 20, bottom edge 22, and inner and outer side edges 24, 26 respectively.

The back member has a pair of vertically extending slots 28 and 30 formed therein. The slots are parallel to one another and to the side edges, and are spaced apart and spaced inwardly from the side edges. As shown in FIG. 1, the slots terminate at locations spaced from the top and bottom edges, and define therebetween a backing panel 32.

The folder further comprises a cover member 34. The cover is formed of transparent plastic material of a flexible nature, for example, that material sold under the trademark MYLAR. The cover member comprises a cover panel 36, and a fold tab 38. The cover panel and fold tab are integrally and hingedly joined along a common fold line 40.

The fold tab is fixedly secured to the rear face 18 of the back member, and has a terminal side edge 42. The terminal side edge is positioned between the slot 28 and the inner side edge 24 of the back panel. The edge 42 serves a function appearing in detail below.

As shown in the drawing, the cover 36 has vertical and longitudinal reference indicia 44 thereon. These reference indicia permit reassembly in similar fashion or assembly at remote locations through contact with other operators having similarly referenced systems of identical likenesses.

The component segments comprise a series of elongated strips 46 formed of transparent plastic. Each has facial characters, such as eyes, nose, etc., inscribed thereon, and each has a vertical inside edge 48, and an outside edge 50. Projecting from the outside edges are pull tabs 52 with identication numerals thereon. The identification numerals also permit remote assembly of a likeness when an appropriate identification has been completed.

In the operation of the system, after the operator is given a general description of a subject by a witness, a preliminary likeness is assembled by sliding the selected component strips 46 through the slots 30 and 28 until the inside edge 48 of each of the strips abuts the terminal side edge 42 of the fold tab, whereby all of the strips are coaligned. Thereafter, substitutions are made as desired by the witness until an acceptable likeness is achieved. The flexibility of the wallet permits viewing of the likeness at different angles and positions, and the cover bears against the assembled strips to prevent disarray. The cover may have a flesh tone tint, and changeable covers may be provided in order to alter the complexion of the assembled likeness.

I claim:

1. In a facial identification system in which a composite of facial features interrelated to form a representation of a subject, the composite being made up of changeable individual feature component segments which partially overlap one another in irregular, layered fashion, the combination of a holder for said segments, and the segments, comprising:

a back member comprising a substantially rectangular panel of opaque, flexible material having opposite front and rear faces, top and bottom edges, and inner and outer side edges;

the panel having a pair of vertically extending slots formed therein in substantially parallel relation to the side edges and spaced inwardly therefrom;

the slots terminating at locations spaced from the top and bottom edges;

the slots defining a backing panel therebetween;

a cover member formed of transparent flexible plastic and including a cover panel and fold tab;

the cover panel and the fold tab being hingedly joined together along a fold line;

the fold tab being fixedly secured to the rear face of the back member and having a terminal side edge located in parallel, inwardly spaced relations to the inner side edge of the back member;

the cover panel being dimensioned to overlie the back member;

the segments being elongated and having inside edges and having outside edges;

the segments being inserted through the slots to overlie the backing panel with the inside edges abutting the terminal side edge of the fold tab, and having pull tabs on the outside edges thereof, said pull tabs projecting outwardly of the backing panel when the inside edges abut the terminal side edge of the fold tab.

2. The invention of claim 1, wherein: the pull tabs have identification means thereon.

3. The invention of claim 1, wherein: the cover panel is tinted in flesh tone.

4. The invention of claim 1, wherein: the cover panel has reference indicia thereon.